(12) United States Patent
Collins et al.

(10) Patent No.: US 11,839,772 B2
(45) Date of Patent: Dec. 12, 2023

(54) REDUNDANT TRACES FOR FLEXIBLE CIRCUITS USED IN AN ENERGY DELIVERY DEVICE

(71) Applicant: Solta Medical Ireland Limited, Dublin (IE)

(72) Inventors: Craig Collins, Woodinville, WA (US); Kurt Duclos, Kenmore, WA (US); Martin Kenney, Bothell, WA (US)

(73) Assignee: Solta Medical Ireland Limited, Dublin (IE)

( * ) Notice: Subject to any disclaimer, the term of this patent is extended or adjusted under 35 U.S.C. 154(b) by 0 days.

(21) Appl. No.: 17/590,027

(22) Filed: Feb. 1, 2022

(65) Prior Publication Data

US 2022/0219005 A1    Jul. 14, 2022

Related U.S. Application Data

(63) Continuation of application No. 16/556,701, filed on Aug. 30, 2019, now Pat. No. 11,273,316.

(60) Provisional application No. 62/725,679, filed on Aug. 31, 2018.

(51) Int. Cl.
| | |
|---|---|
| *A61N 1/40* | (2006.01) |
| *H05K 1/18* | (2006.01) |
| *G01K 7/24* | (2006.01) |
| *H05K 1/02* | (2006.01) |

(52) U.S. Cl.
CPC ............. *A61N 1/40* (2013.01); *G01K 7/24* (2013.01); *H05K 1/0277* (2013.01); *H05K 1/189* (2013.01); *H05K 2201/10151* (2013.01); *H05K 2201/10196* (2013.01)

(58) Field of Classification Search
CPC .......... A61N 1/40; G01K 7/24; H05K 1/0277; H05K 1/189; H05K 2201/10151; H05K 2201/10196
USPC ......................................................... 604/154
See application file for complete search history.

(56) References Cited

U.S. PATENT DOCUMENTS

| | | | |
|---|---|---|---|
| 9,161,802 B2* | 10/2015 | Przybyszewski | ...... A61B 18/14 |
| 9,329,993 B2 | 5/2016 | Zipperer et al. | |
| 9,600,112 B2 | 3/2017 | Zhang et al. | |
| 2008/0200969 A1* | 8/2008 | Weber | ....................... A61N 1/06 374/E13.002 |
| 2013/0165925 A1* | 6/2013 | Mathur | ..................... A61N 1/05 606/41 |

* cited by examiner

*Primary Examiner* — Binh B Tran
(74) *Attorney, Agent, or Firm* — Thompson Hine LLP

(57) ABSTRACT

Energy delivery devices with a flexible circuit. The energy delivery devices may be used in the treatment of human tissue, and the flexible circuit move or flex during use. The flexible circuit may include an electronic component and a trace connected with the electronic component. The trace may have a plurality of sections that provide parallel current paths over a portion of the trace. Alternatively, the flexible circuit may include a plurality of traces that are connected with the terminal of the electronic component to provide parallel current paths over their entire length to the terminal of the electronic component. These redundant parallel current paths improve device reliability.

18 Claims, 9 Drawing Sheets

REDUNDANT TRACES FOR FLEXIBLE CIRCUITS USED IN AN ENERGY DELIVERY DEVICE

CROSS-REFERENCE TO RELATED APPLICATIONS

This application is a continuation of application Ser. No. 16/556,701, filed Aug. 30, 2019, which claims the benefit of U.S. Provisional Application No. 62/725,679, filed Aug. 31, 2018, the content of each of which is fully incorporated by reference herein in its entirety.

FIELD OF THE INVENTION

The invention generally relates to flexible circuits for an energy delivery device used to treat tissue with electromagnetic energy.

BACKGROUND

Certain types of energy delivery devices are capable of treating a patient's tissue with electromagnetic energy. These energy delivery devices, which emit electromagnetic energy in different regions of the electromagnetic spectrum for tissue treatment, may be used to treat a multitude of diverse skin conditions. For example, the energy delivery device may non-ablatively and non-invasively treat a skin condition or other type of tissue condition.

One variety of these energy delivery devices emits high frequency electromagnetic energy in the radio-frequency (RF) band of the electromagnetic spectrum. The high frequency energy may be used to treat skin tissue by passing high frequency energy through a surface of the skin, while actively cooling the skin to prevent damage to the skin's epidermal layer closer to the skin surface. The high frequency energy heats tissue beneath the epidermis to a temperature sufficient to denature collagen, which causes the collagen to contract and shrink and, thereby, tighten the tissue. Treatment with high frequency energy also causes a mild inflammation. The inflammatory response of the tissue causes new collagen to be generated over time (between three days and six months following treatment), which results in further tissue contraction.

Typically, energy delivery devices include a treatment tip that is placed in contact with, or proximate to, the patient's skin surface and that emits electromagnetic energy that penetrates through the skin surface and into the tissue beneath the skin surface. The non-patient side of the energy delivery device, such as an electrode for high frequency energy, in the treatment tip may be sprayed with a coolant or cryogen spray. Heat is conducted from the warmer tissue to the cooler treatment tip, which cools tissue to a shallow depth beneath the skin surface. A controller may trigger the coolant spray based upon an evaluation of the temperature readings received as feedback from temperature sensors in the treatment tip.

The cryogen spray may be used to pre-cool superficial tissue before delivering the electromagnetic energy. When the electromagnetic energy is delivered, the superficial tissue that has been cooled is protected from thermal effects. The target tissue that has not been cooled or that has received nominal cooling will warm up to therapeutic temperatures resulting in the desired therapeutic effect. The amount or duration of pre-cooling can be used to select the depth of the protected zone of untreated superficial tissue. After the delivery of electromagnetic energy has concluded, the cryogen spray may also be employed to prevent or reduce heat originating from treated tissue from conducting upward and heating the more superficial tissue that was cooled before treatment with the electromagnetic energy.

The electrode and temperature sensors may be arranged on a flexible circuit inside the treatment tip. The temperature sensors are used to measure the temperature at the interface between the flexible circuit and the patient's skin. The flexible circuit may include a polyimide layer and traces containing a conductive material that provide conductive paths routed over the polyimide layer to and from the electrode and temperature sensors. In the assembly of the treatment tip, the flexible circuit is folded about a rigid support member with the electrode facing a window in the tip housing. During patient treatment, the flexible circuit experiences repeated flexure when the tip is pressed against the patient's skin numerous times. The repeated flexure may cause traces to crack and fail, especially at creases at which the flexible circuit is folded and that may experience locally-high stress. Trace failure results in the premature failure of the entire treatment tip. For example, trace failure may interrupt the ability to receive readings from the temperature sensors.

Improved flexible circuits for an energy delivery device used to treat tissue with electromagnetic energy are needed.

SUMMARY

In an embodiment, an apparatus includes an energy delivery device with a flexible circuit. The flexible circuit includes an electronic component and a trace connected with the electronic component. The trace has a plurality of sections that provide parallel current paths over a portion of the trace.

In an embodiment, an apparatus includes an energy delivery device with a flexible circuit. The flexible circuit includes an energy delivery device including a flexible circuit, the flexible circuit including an electronic component and a plurality of traces connected with a terminal of the electronic component to provide parallel current paths to the terminal of the electronic component.

In embodiments of the invention, two or more redundant electrically-conductive traces, or traces with two or more redundant electrically-conductive sections or segments, may be routed to each side of one or more thermal sensors (e.g., thermistors) on a treatment tip, which may be attached to or integral with a handpiece. The treatment tip and handpiece may be used as an energy delivery device to apply electromagnetic energy to a patient. The traces, or the segments of the traces, may provide electrical redundancy in the event of trace fracture or failure and, therefore, enhanced reliability.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention. In the drawings, like reference numerals are used to indicate like parts in the various views.

DETAILED DESCRIPTION

Figure 1:
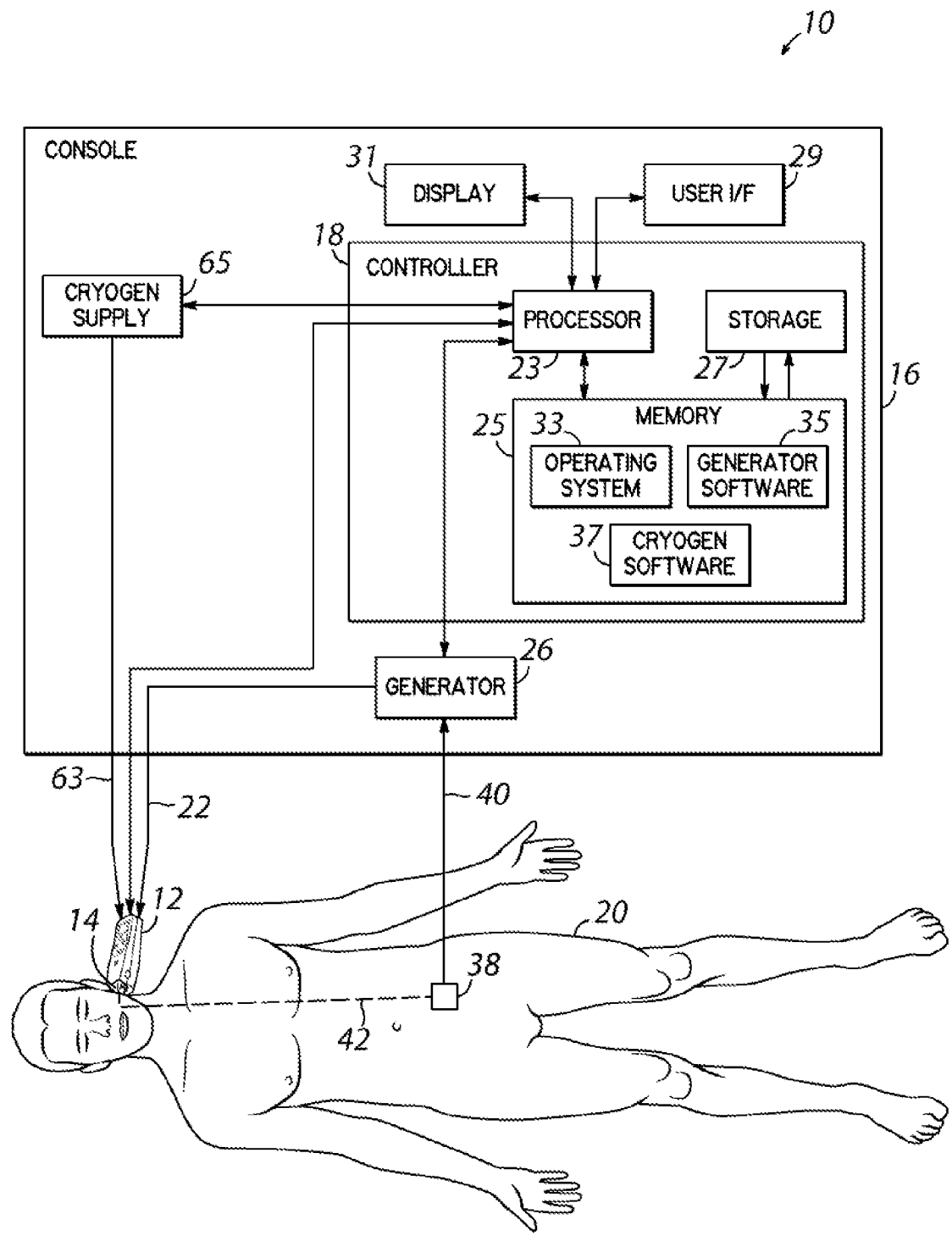
FIG. 1 is a diagrammatic view of a treatment system with a handpiece, a treatment tip, a console, and a generator.
Figure 2:
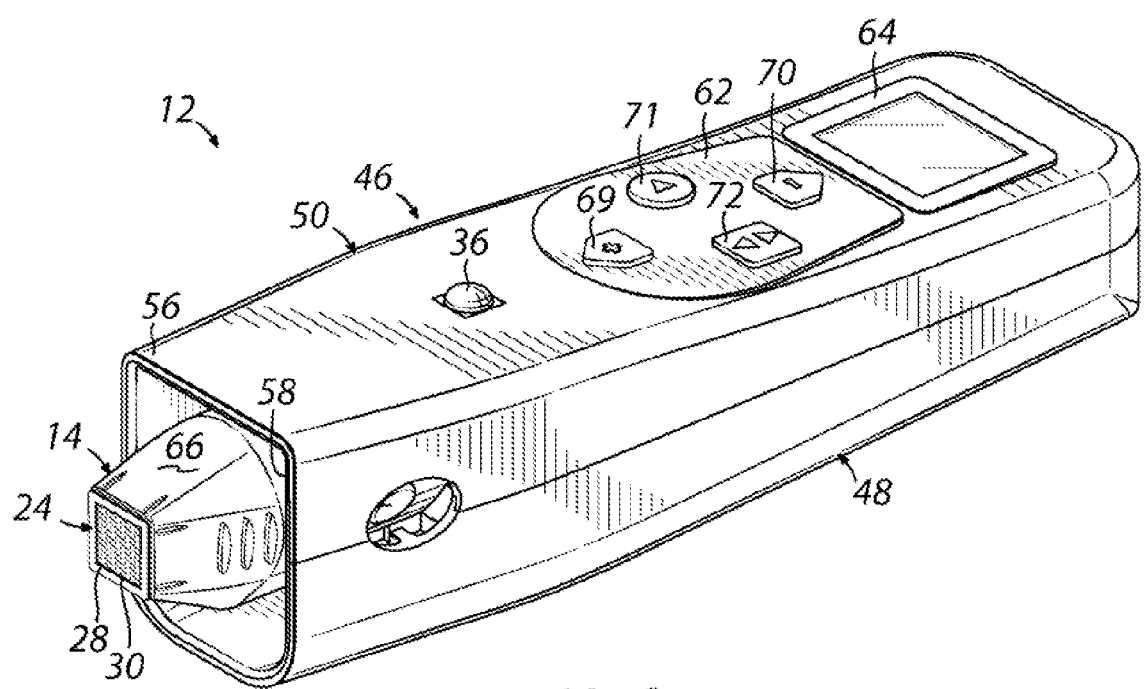
FIG. 2 is a perspective view of an assembly consisting of an embodiment of the handpiece and treatment tip for use with the treatment system of FIG. 1.
Figure 3:
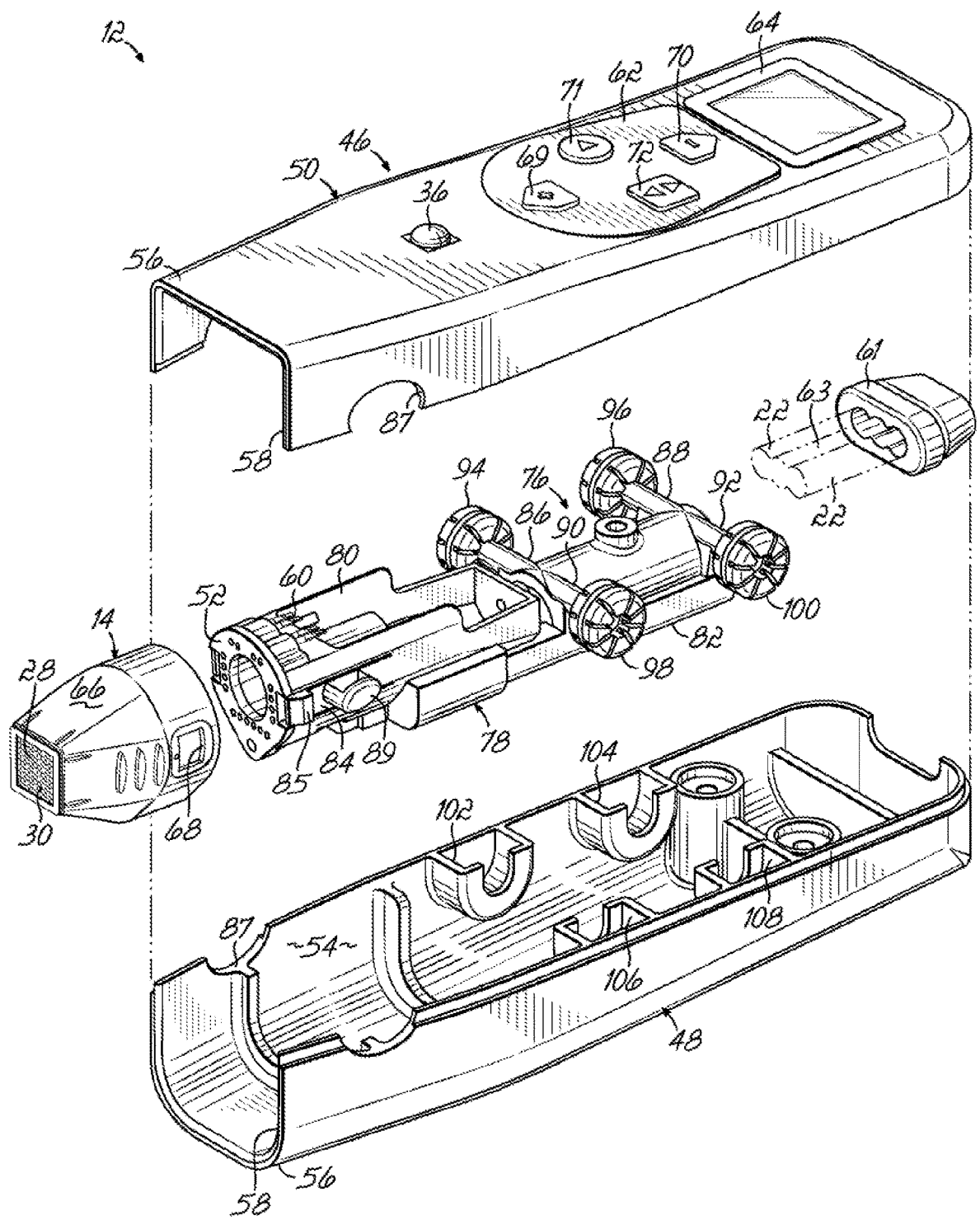
FIG. 3 is an exploded view of the assembly of FIG. 2.

Referring now to the drawings, FIGS. 1-7 disclose a treatment apparatus 10 that generally includes a handpiece 12, a treatment tip 14 that may be coupled in a removable and releasable manner with the handpiece 12, a console generally indicated by reference numeral 16, and a system controller 18. The system controller 18, which is incorporated into the console 16, orchestrates the global operation of the different individual components of the treatment apparatus 10. Under the control of the system controller 18 and any operator interaction with the system controller 18 at the console 16 and with controls at the handpiece 12, the treatment apparatus 10 is adapted to deliver electromagnetic energy in a high frequency band of the electromagnetic spectrum to a region of a patient's tissue. The electromagnetic energy, which may be delivered non-invasively and non-ablatively, heats the tissue to a targeted temperature range over a tissue depth. The elevation in temperature may produce for example, changes in collagen fibers that achieve a desired treatment result, such as removing or reducing wrinkles and otherwise tightening the skin to thereby improve the appearance of a patient 20 receiving the treatment.

The treatment tip 14 may provide, either alone or in combination with the handpiece 12, an energy delivery member that includes a treatment electrode 24. In a representative embodiment, the treatment electrode 24 may be arranged on a flexible circuit 74 that includes an electrically-insulating substrate 30 composed of a non-conductive dielectric material and a region 28 composed of an electrical conductor carried on the electrically-insulating substrate 30. The electrically-insulating substrate 30 may have a contact side 32 that is placed in contact with a patient's skin surface and a non-contact side 34 that is opposite from the contact side 32. The conductor region 28 of the treatment electrode 24 is physically carried on the non-contact side 34 of the substrate 30 and is therefore separated by the substrate 30 from the skin surface during treatment.

The substrate 30 of the flexible circuit 74 may include a thin flexible base polymer film with thin conductive leads or traces 49. Some of the leads 49 may electrically couple the conductor region 28 with one or more contact pads 57. The base polymer film of substrate 30 may be, for example, polyimide or another material with a relatively high electrical resistivity and a relatively high thermal conductivity. The traces 49 and contact pads 57 may contain copper or another conductor characterized by a relatively high electrical conductivity. The traces 49 and contact pads 57 may be formed by depositing a layer of the conductor on the substrate 30 and patterning the conductor layer with lithography and etching processes. Instead of the representative single conductor region 28, the conductor region 28 providing the treatment electrode 24 may be segmented into plural individual electrodes that can be individually powered to sequentially deliver electromagnetic energy to the tissue.

The treatment electrode 24 is electrically coupled through the traces 49 and contact pads 57 by a set of insulated and shielded conductors 22 that extend from the handpiece 12 to the generator 26 at the console 16. The generator 26 is configured to generate the electromagnetic energy used in the treatment to impart a therapeutic effect by heating target tissue beneath the patient's skin surface. The generator 26, which may have the form of a high frequency power supply, is equipped with an electrical circuit operative to generate high frequency electrical current, typically in the radio-frequency (RF) band of the electromagnetic spectrum. The electrical circuit in the generator 26 converts a line alternating current voltage into drive signals for the treatment electrode 24. The drive signals have parameters (e.g., energy content and duty cycle) appropriate for the amount of power and the mode of operation that have been selected by the treating clinician. In alternative embodiments, the treatment apparatus 10 may be configured to deliver energy in the infrared band, microwave band, or another high frequency band of the electromagnetic spectrum, rather than within the RF band, to the patient's tissue.

The system controller 18 may include at least one processor 23 coupled to a non-transitory memory 25. The at least one processor 23 may represent one or more microprocessors, and the memory 25 may represent the random access memory (RAM) comprising the main storage of system controller 18, as well as any supplemental levels of memory, e.g., cache memories, non-volatile or backup memories (e.g., programmable or flash memories), read-only memories, etc. In addition, memory 25 may be considered to include memory storage physically located elsewhere in system controller 18, e.g., any cache memory in a processor 23, as well as any storage capacity used as a virtual memory, e.g., as stored on a mass storage device 27 or another computer (not shown) coupled to system controller 18 via a network.

The system controller 18 also typically receives a number of inputs and outputs for communicating information externally. For interface with a user or operator, system controller 18 typically includes one or more user input devices (e.g., a keyboard, a mouse, a trackball, a joystick, a touch screen, a keypad, a stylus, discrete buttons, and/or a microphone, among others) in the form of a user interface 29. The user interface 29 may be used to deliver instructions to the system controller 18 to adjust the generator 26 and to establish treatment settings based upon operator input at the handpiece 12. System controller 18 may also include a display 31 (e.g., a LED or LCD display panel, among others).

System controller 18 operates under the control of an operating system 33, and executes or otherwise relies upon various computer software applications, components, programs, objects, modules, data structures, etc. In general, the routines executed by the system controller 18 to operate the treatment apparatus 10, whether implemented as part of an operating system or a specific application, component, program, object, module or sequence of instructions, will be referred to herein as "computer program code." The computer program code typically comprises one or more instructions that are resident at various times in various memory and storage devices in a computer, and that, when read and executed by one or more processors in a computer, causes that computer to perform the steps necessary to execute steps or elements embodying the various aspects of the embodiments of the invention.

The system controller 18 includes digital and/or analog circuitry that interfaces the processor 23 with the generator 26 for regulating the power delivered from the generator 26 to the treatment electrode 24. Generator software 35 resides as an application (i.e., program code) in the memory 25 and is executed by the processor 23 in order to issue commands that control the operation of the generator 26. The system controller 18 includes digital and/or analog circuitry that interfaces the processor 23 with a cryogen supply 65, such as a system configured to deliver pressurized cryogen to a control valve (not shown) at the handpiece 12 and to control the control valve for regulating the cryogen delivered to the treatment electrode 24. Cryogen software 37 resides as an application (i.e., program code) in the memory 25 and is executed by the processor 23 in order to issue commands that control the operation of the cryogen supply 65 and control valve. Other types of cooling, such as conductive cooling, may be employed, and cooling, while preferable, may be optional.

During a tissue treatment involving the treatment electrode 24, the substrate 30 is arranged between the conductor region 28 and the skin surface of the patient. Electromagnetic energy may be transmitted in a transcutaneous manner from the conductor region 28 through the thickness of substrate 30 and across the surface area of the portion to the tissue by capacitively coupling with the tissue of the patient 20.

Figure 4:
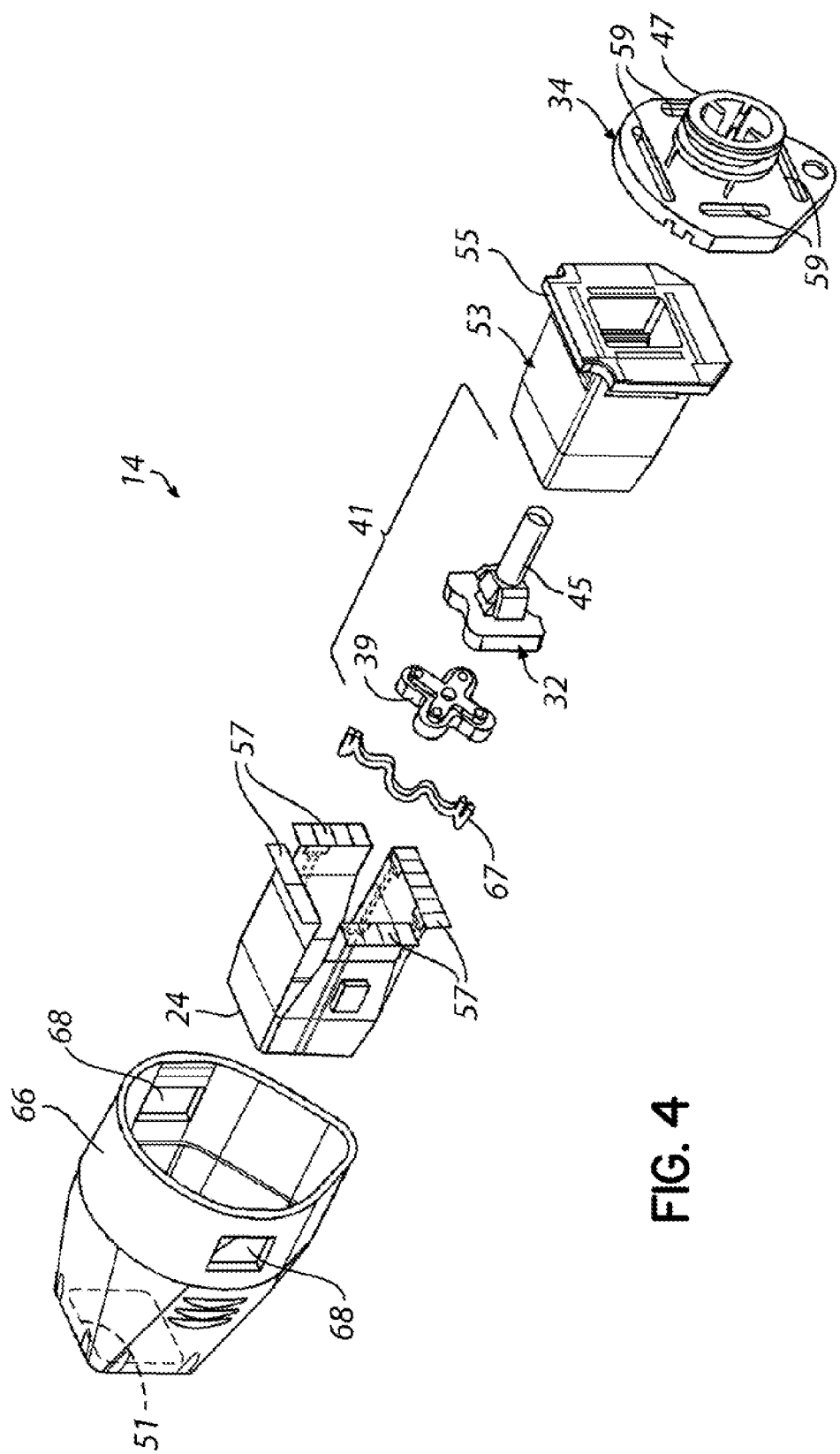
FIG. 4 is an exploded view of the treatment tip of FIGS. 2, 3 in which the flexible circuit is shown in a folded condition.

As best shown in FIG. 4, the treatment tip 14 includes temperature sensors 44, such as thermistors, that are located on the non-contact side 34 of the substrate 30 that is not in contact with the patient's skin surface. Typically, the temperature sensors 44 are arranged about the perimeter of the conductor region 28 of the treatment electrode 24. Temperature sensors 44 are constructed to detect the temperature of the treatment electrode 24 and/or treatment tip 14, which may be representative of the temperature of the treated tissue. The measured temperature reflects the temperature of the treated tissue and may be used as feedback in a control loop controlling energy delivery and/or cooling of the skin surface. The treatment tip 14 may also include pressure sensors (not shown) for detecting physical contact between the treatment electrode 24 and the skin surface of the patient 20.

An activation button 36, which is accessible to the operator from the exterior of the handpiece 12, is configured to be actuated to close a switch in a normally open circuit with the generator 26. The closed circuit energizes the treatment electrode 24. Actuation of the activation button 36 triggers delivery of the high frequency energy over a short timed delivery cycle to the target tissue. After a fixed amount of time has elapsed, the delivery of high frequency energy from the treatment electrode 24 to the tissue at the treatment site is discontinued. In a stamping mode of operation, the handpiece 12 is manipulated to position the treatment tip 14 near a different treatment site on the skin surface and another cycle of high frequency energy is delivered to the patient's tissue. This process may be repeated for an arbitrary number of treatment sites.

High frequency electrical current flowing between the treatment electrode 24 and the patient 20 is concentrated at the skin surface and the underlying tissue across the contacting surface area of the portion of the treatment electrode 24. Capacitive coupling of the high frequency electromagnetic energy relies on energy transfer from the conductor region 28 through the dielectric material of the substrate 30 to create an electric field across the surface area where the treatment electrode 24 contacts the patient's body. The time-varying electric field induces electrical currents within the surrounding tissue beneath the skin surface.

Because of the natural resistance of tissue to electrical current flow, volumetric heating results within the tissue. The volumetric heating delivers a therapeutic effect to the tissue near the treatment site. For example, heating to a temperature of 50° C. or higher may contract collagen, which may result in tissue tightening or another aesthetic effect to improve the patient's appearance. The heating depth in the tissue is based upon the size and geometry of the treatment electrode 24 and, contingent upon the selection and configuration of the treatment tip 14, can be controlled to extend from a few hundred micrometers beneath the skin surface to several millimeters.

A non-therapeutic passive return electrode 38 may be used to electrically couple the patient 20 with the generator 26. During patient treatment, the high frequency current flows from the treatment electrode 24 through the treated tissue and the intervening bulk of the patient 20 to the return electrode 38 and then to the generator 26 through conductors inside a return cable 40 to define a closed circuit or current path 42. The return electrode 38 is physically attached by, for example, an adhesive bond to a site on the body surface of the patient 20, such as the patient's back.

The surface area of the return electrode 38 in contact with the patient 20 may be relatively large in comparison with the surface area of the treatment electrode 24. Consequently, at the tissue adjacent to the return electrode 38, the current density flowing from the patient 20 to the return electrode 38 is relatively low in comparison with the current density flowing from the treatment electrode 24 to the patient 20. Because negligible heating is produced at its attachment site to the patient, a non-therapeutic effect is created in the tissue adjacent to the return electrode 38.

Although the treatment electrode 24 and the return electrode 38 are representatively configured for the delivery of monopolar high frequency energy, the treatment electrode 24 may be configured to deliver bipolar high frequency energy. The modifications to the treatment apparatus 10 required to deliver bipolar high frequency energy are familiar to a person having ordinary skill in the art. For example, the return electrode 38 may be eliminated from the treatment apparatus 10 and a bipolar type of treatment electrode substituted for the monopolar treatment electrode 24.

With continued reference to FIGS. 1-7, the handpiece 12 is constructed from a housing 46 that includes a body 48, a cover 50 assembled by conventional fasteners with the body 48, and an electrical/fluid interface 52 for the treatment tip 14. The housing 46 may be fabricated by an injection molding process using a suitable polymer resin as a construction material. The body 48 and cover 50 constitute shell halves that are integrally fastened together as an assembly. The housing 46 encloses an interior cavity 54 bounded on one side by an interior surface of the body 48 and bounded on the other side by an interior surface of the cover 50. After the body 48 and cover 50 are assembled, the handpiece 12 has a smoothly contoured shape suitable for gripping and manipulation by an operator. The operator maneuvers the treatment tip 14 and treatment electrode 24 to a location proximate to the skin surface and, typically, to place the treatment electrode 24 in proximity with the skin surface.

The housing 46 includes a nose 56 and a window 58 in the nose 56 that is sized for the insertion and removal of the treatment tip 14. The electrical/fluid interface 52 is disposed between the window 58 and the interior cavity 54 enclosed inside the housing 46. The treatment tip 14 is sized to be inserted through the window 58 and configured to be physically engaged with the handpiece 12, as described below. In the engaged state, the contact pads carried on the substrate 30 of the treatment electrode 24 establish respective electrical connections with complementary electrical contacts 60 (FIG. 3), such as pogo pins, carried by the electrical/fluid interface 52 of the handpiece 12. These electrical contacts 60 are electrically coupled with one or more of the conductors 22 that extend from the handpiece 12 to the generator 26 and system controller 18.

The handpiece 12 may include a control panel 62 and a display 64 that may be carried by the cover 50. The control panel 62 may include various controls, such as controls 69, 70 used to respectively increase and reduce the treatment setting and controls 71, 72 that respectively enable and disable the controls 69, 70. The display 64 may be used to display information including, but not limited to, energy delivered, tissue impedance, duration, and feedback on procedure technique. The availability of the information displayed on the display 64 may conveniently eliminate the need to display identical information at the console 16 or may duplicate information displayed at the console 16. By displaying information at the handpiece 12, the operator can focus on the procedure without diverting his attention to glance at information displayed by the display on the console 16. In one embodiment, the display 64 may constitute a thin, flat liquid crystal display (LCD) comprised of a light source or reflector and an arbitrary number of color or monochrome pixels arrayed in front of the light source or reflector. A driver circuit (not shown) is provided to control the operation of the display 64.

The treatment tip 14 includes a rigid outer shell 66 and a nipple 34 that is coupled with the open rearward end of the outer shell 66 to surround an interior cavity. A fluid delivery member 41 is configured to deliver a spray of a cryogen or similar coolant from a nozzle 39 onto the electrode 24. Extending rearwardly from a central fluid coupling member 32 is a conduit 45 having a lumen defining a fluid path that conveys a flow of the coolant to the nozzle 39. The coolant is pumped from a coolant supply (FIG. 1) through tubing that is mechanically coupled with a fitting 47 formed on the nipple 34 and hydraulically coupled with the lumen of the conduit 45.

The electrode 24 is exposed through a window 51 defined in a forward open end of the outer shell 66. The rearward end of the support member 53 includes a flange 55 used to couple the support member 53 to the nipple 34. The flexible substrate is wrapped or folded about the support member 53 such that the contact pads 57 are exposed through slots 59 defined in the nipple 34. A support arm 67 bridges the window 51 for lending mechanical support to the flexible substrate 30.

The treatment tip 14 includes openings 68 defined on diametrically opposite sides of the outer shell 66. The openings 68 are used to temporarily secure the treatment tip 14 with the handpiece 12 in advance of a patient treatment procedure. The handpiece 12 includes a control valve used to deliver a cryogen spray to the treatment electrode 24 for controlling the temperature of the treatment electrode 24. A line 63 connects the control valve with a cryogen supply 65.

One purpose of the cryogen spray is to pre-cool the patient's epidermis, before powering the treatment electrode 24, by heat transfer between the treatment electrode 24 and the skin surface. The cooling creates a reverse thermal gradient in the tissue such that the temperature of the tissue at and near the skin surface is cooler than the temperature of the tissue deeper within the epidermis or dermis. As a result, the high frequency energy delivered to the tissue fails to heat all or a portion of the patient's epidermis to a temperature sufficient to cause significant epidermal thermal damage. Depths of tissue that are not significantly cooled by pre-cooling will warm up to therapeutic temperatures, which cause a desired therapeutic effect. The amount and/or duration of pre-cooling may be used to select the protected depth of untreated tissue. The cryogen delivered by the control valve may also be used to cool portions of the tissue during and/or after heating by the high frequency energy transferred from the treatment electrode 24. Post-cooling may prevent or reduce heat delivered deeper into the tissue from conducting upward and heating shallower tissue regions, such as the epidermis, to temperatures which could thermally damage shallower tissue regions even though external energy delivery to the targeted tissue has ceased.

Various duty cycles of cooling and heating that rely on cooling and high frequency energy transfer from the treatment electrode 24 are utilized contingent upon the type of treatment and the desired type of therapeutic effect. The cooling and heating duty cycles may be controlled and coordinated by operation of the system controller 18 and control valve. Suitable cryogens include low boiling point fluids, but are not limited to, R134a (1,1,1,2-tetrafluoroethane) refrigerant, liquid nitrogen, HFO-1234ze (1,3,3,3-tetrafluoropropene) refrigerant, and R152a (1,1-difluoroethane) refrigerant. Heat can be extracted from the treatment electrode 24 by virtue of evaporative cooling of the cryogen, which lowers the temperature of the treatment electrode 24.

Figure 5:
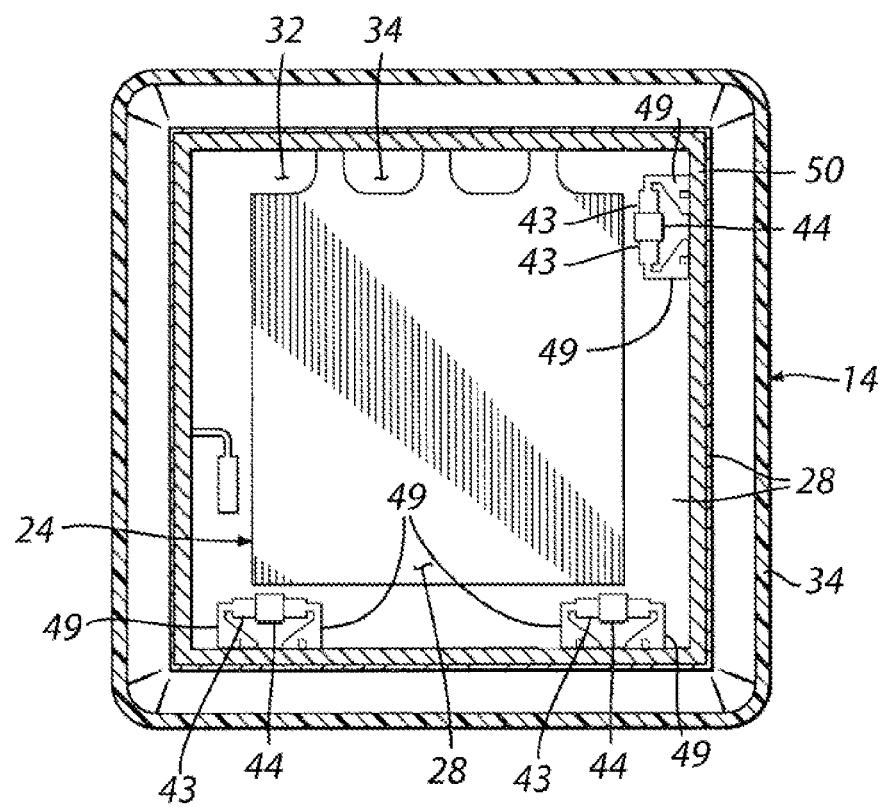
FIG. 5 is a rear view of the treatment tip of FIGS. 2, 3 showing an electrode and temperature sensors on the flexible circuit.
Figure 6:
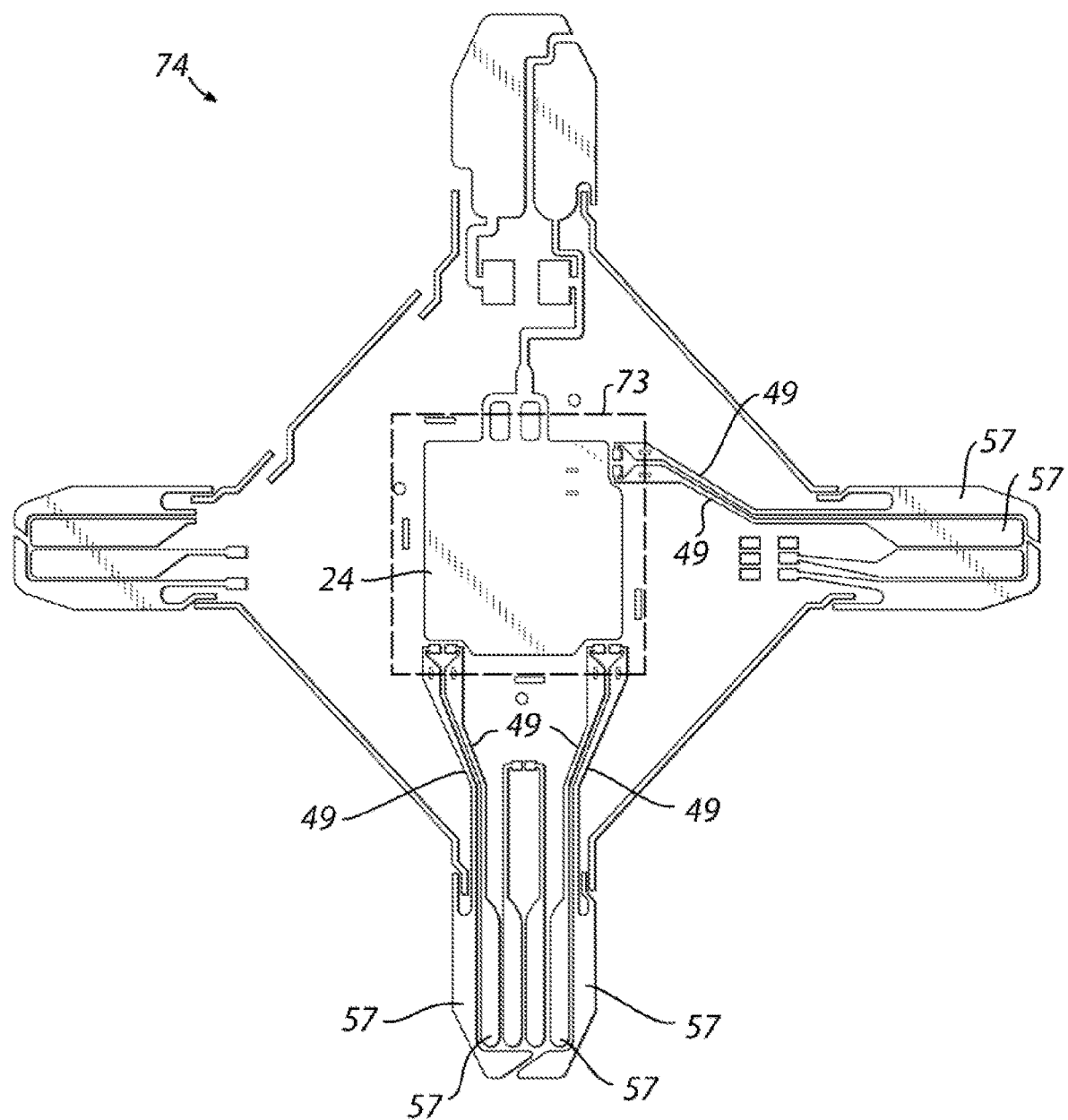
FIG. 6 is a rear view in which the flexible circuit of FIG. 4 is shown in an unfolded condition.
Figure 7:
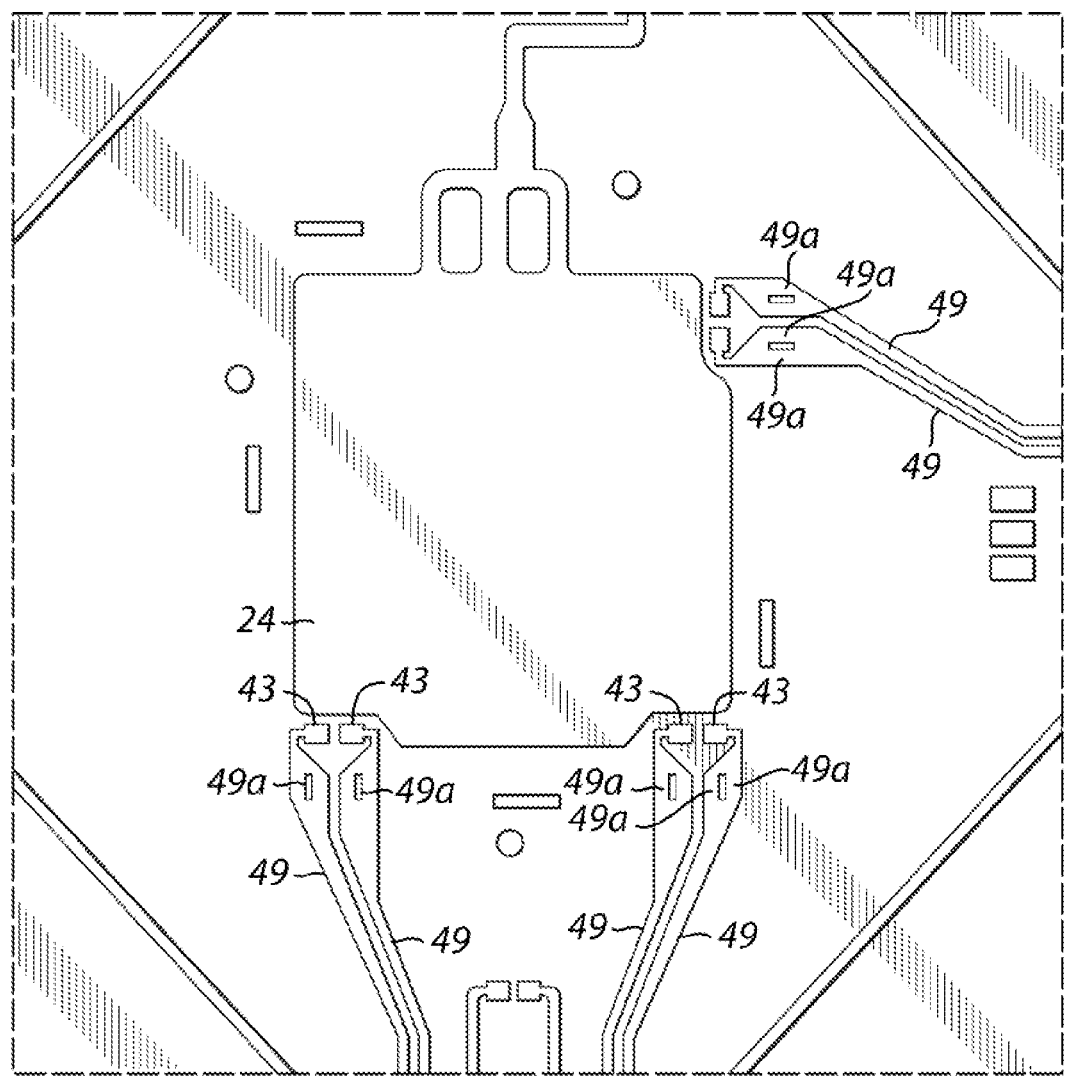
FIG. 7 is an enlarged view of a portion of FIG. 6.

With specific reference to FIGS. 5-7, the flexible circuit 74 in the treatment tip 14 includes the treatment electrode 24 arranged on the electrically-insulating substrate 30 and the temperature sensors 44 that are surface mounted to the electrically-insulating substrate 30. The flexible circuit 74 is a non-rigid variety of printed circuit board that includes the traces 49. The temperature sensors 44 are electrically coupled by conductive traces 49 with the contact pads 57, which are used to supply direct current (DC) voltages from the system controller 18 through the electrical wiring to the temperature sensors 44.

Each of the temperature sensors 44 has terminals that are each attached or connected to attachment pads 43 to provide a mechanical connection with the electrically-insulating substrate 30 and an electrical connection with one of the traces 49 that terminates at each attachment pad 43. For example, package leads from the temperature sensor 44 may provide terminals in which one of the terminals is attached to one of a pair of attachment pads 43 and the other of the terminals is attached to the other of the pair of attachment pads 43. Each trace 49 is routed from its respective attachment pad 43 to one of the contact pads 57 arranged on one of the flaps of the flexible circuit 74.

Each of the traces 49 is split over a portion of its length into multiple sections 49a that supply parallel current paths for communicating with the associated temperature sensor 44. The trace sections 49a are arranged adjacent to each other along the length of the traces 49. A crease or fold line 73 created when the flexible circuit 74 is wrapped about the support member 53 is diagrammatically indicated by the dashed rectangle in FIG. 6. The trace sections 49a cross the fold line 73 when the flexible circuit 74 is folded over the support member during assembly of the treatment tip 14 such that the trace sections 49a separate on one side of the fold line and converge back together on an opposite side of the fold line 73. The respective longitudinal axes of the trace sections 49a of the traces 49 may be oriented to intersect the fold line 73 at a right angle (i.e., perpendicular to the fold line 73) or substantially at a right angle (i.e., transverse to the fold line 73). The trace sections 49a are separated by a central open slit or slot of a given length. The width of the slot and/or the width of the trace sections 49a may be selected to enhance the resistance to cracking and crack propagation. The fold line 73 extends across the open slot transverse to its length.

The redundancy in the current paths provided by the trace sections 49a of each trace 49 furnishes a mechanism by which one of the trace sections 49a of the trace 49 may fail due to, for example, the propagation of a crack generated by flexure and electrically open, while the other of the trace sections 49a of the trace 49 maintains a closed circuit. Differences in the local stresses in the folded flexible circuit 74, among other factors, may cause differences in the failure rate of the different trace sections 49a over the operational lifetime of the treatment tip 14.

The number of individual trace sections 49a in the representative embodiment is two (2), although more than two trace sections 49a may be incorporated into each trace 49 to provide more than two parallel and redundant current paths in the traces 49 leading to and from the sides of the associated temperature sensor 44 (e.g., the positive and negative terminals of a thermistor). The aspect ratio (e.g., width and thickness) of the traces 49 may be selected to provide additional resistance to crack propagation and to lessen the failure probability due to cracking. In some embodiments, the number of trace sections 49a may be at least two (2), or at least three (3), or at least four (4), or at least five (5), or at most five (5), or at most four (4), or at most three (3), or at most two (2) per trace 49. In some embodiments, each trace 49 may include two (2), or three (3), or four (4), or five (5) trace sections 49a.

Figure 8:
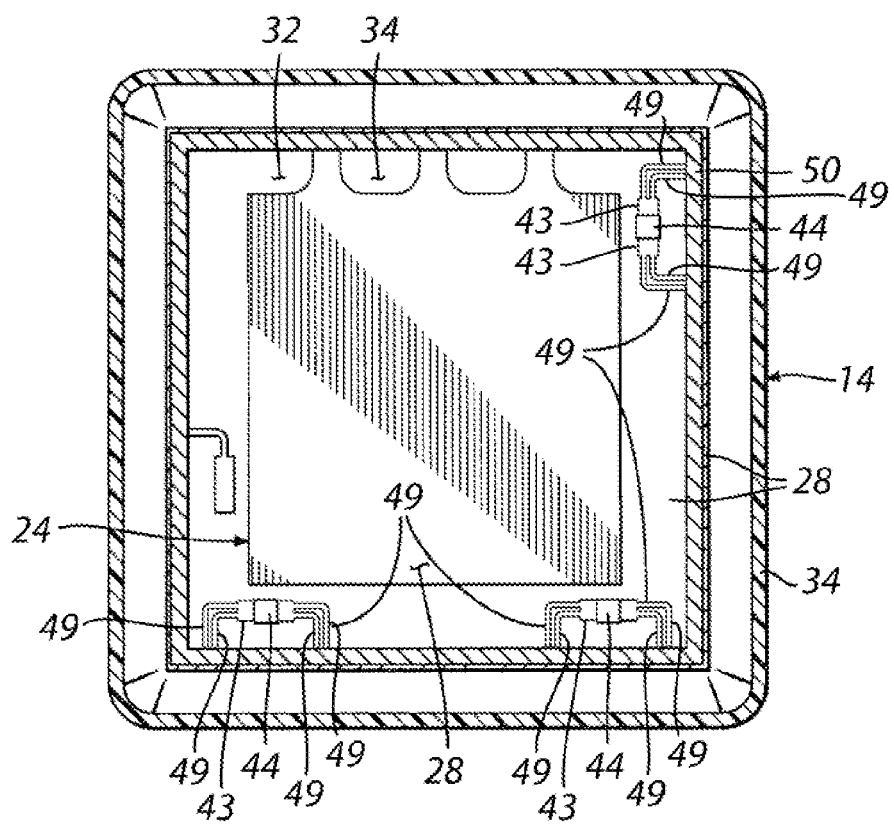
FIG. 8 is a rear view of an assembled treatment tip showing an electrode and temperature sensors on a flexible circuit in accordance with alternative embodiments.
Figure 9:
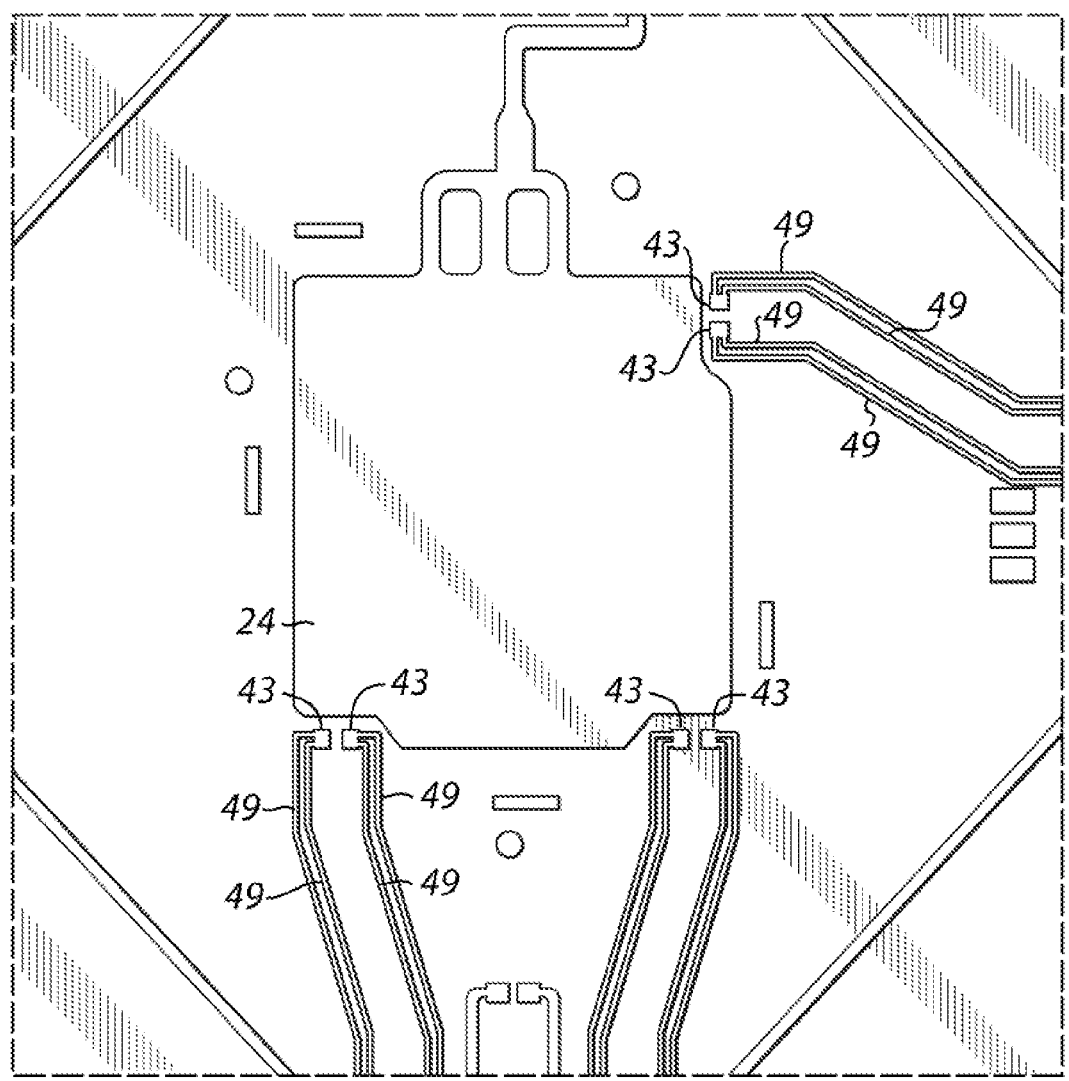
FIG. 9 is an enlarged view similar to FIG. 7 showing a portion of the flexible circuit of FIG. 8 in an unfolded condition.

With reference to FIGS. 8, 9 and in accordance with embodiments of the invention, each attachment pad 43 may be connected with multiple traces 49 that extend from the attachment pad 43 to one of the contact pads 57 arranged on the flaps of the flexible circuit 74. The multiple traces 49 provide redundancy in the circuit path similar to the trace sections 49a (FIGS. 6, 7). The traces 49 are routed to cross the fold line 73 (FIG. 6) when the treatment tip 14 is assembled and, in particular, may have longitudinal axes that are oriented to intersect the fold line at a right angle (i.e., perpendicular to the fold line 73) or substantially at a right angle (i.e., transverse to the fold line 73). Each of the traces 49 connected with one of the attachment pads 43 extend along its full length from the associated attachment pad 43 to the associate contact pad 57 such that the parallel current paths are separated over their entire length and lack trace sections.

References herein to terms such as "vertical," "horizontal," etc. are made by way of example, and not by way of limitation, to establish a frame of reference. It is understood that various other frames of reference may be employed for describing the invention without departing from the spirit and scope of the invention. It is also understood that features of the invention are not necessarily shown to scale in the drawings. Furthermore, to the extent that the terms "composed of", "includes", "having", "has", "with", or variants thereof are used in either the detailed description or the claims, such terms are intended to be inclusive and open-ended in a manner similar to the term "comprising."

References herein to terms modified by language of approximation, such as "about", "approximately", and "substantially", are not to be limited to the precise value specified. The language of approximation may correspond to the precision of an instrument used to measure the value and, unless otherwise dependent on the precision of the instrument, may indicate +/−10% of the stated value(s).

A feature "connected" or "coupled" to or with another element may be directly connected or coupled to the other element or, instead, one or more intervening elements may be present. A feature may be "directly connected" or "directly coupled" to another element if intervening elements are absent. A feature may be "indirectly connected" or "indirectly coupled" to another element if at least one intervening element is present.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. An apparatus comprising:
an energy delivery device including a flexible circuit, the flexible circuit including an electronic component having a first terminal and a second terminal, a first trace connected with the first terminal of the electronic component, and a second trace connected to the second terminal of the electronic component, the first trace having a portion with a plurality of parallel sections that provide a first set of parallel current paths over the portion of the first trace, and the second trace having a portion with a plurality of parallel sections that provide a second set of parallel current paths over the portion of the second trace.

2. The apparatus of claim 1 wherein the electronic component is a temperature sensor.

3. The apparatus of claim 2 wherein the temperature sensor is a thermistor.

4. The apparatus of claim 1 further comprising:
a support member,
wherein the flexible circuit is folded about a surface of the support member along a fold line, and each parallel section of the portion of the first trace extends along a respective longitudinal axis that crosses the fold line.

5. The apparatus of claim 4 wherein the longitudinal axis of each parallel section of the portion of the first trace is oriented transverse to the fold line.

6. The apparatus of claim 1 wherein the energy delivery device is included in a treatment tip that is configured to be detachably coupled with a handpiece.

7. The apparatus of claim 1 wherein the flexible circuit includes a treatment electrode configured to emit high frequency electromagnetic energy in the radio-frequency band of the electromagnetic spectrum, and the first trace connects the first terminal of the electronic component with the treatment electrode.

8. The apparatus of claim 1 wherein the flexible circuit includes a first attachment pad and a second attachment pad, the first terminal of the electronic component is attached to the first attachment pad, the first trace terminates at the first attachment pad, the second terminal of the electronic component is attached to the second attachment pad, and the second trace terminates at the second attachment pad.

9. The apparatus of claim 8 wherein the flexible circuit includes a first contact pad and a second contact pad, the first trace extends from the first attachment pad to the first contact pad, the first contact pad is configured to establish an external contact with the first terminal, the second trace extends from the second attachment pad to the second contact pad, and the second contact pad is configured to establish an external contact with the second terminal.

10. An apparatus comprising:
an energy delivery device including a flexible circuit, the flexible circuit including an electronic component having a first terminal, a second terminal, a first plurality of traces, and a second plurality of traces, the first plurality of traces connected with the first terminal of the electronic component to provide a first set of parallel current paths to the first terminal of the electronic component, and the second plurality of traces connected with the second terminal of the electronic component to provide a second set of parallel current paths to the second terminal of the electronic component.

11. The apparatus of claim 10 wherein the electronic component is a temperature sensor.

12. The apparatus of claim 11 wherein the temperature sensor is a thermistor.

13. The apparatus of claim 10 further comprising:
a support member,
wherein the flexible circuit is folded about a surface of the support member along a fold line, and each of the first plurality of traces extends along a respective longitudinal axis that crosses the fold line.

14. The apparatus of claim 13 wherein the longitudinal axis of each of the first plurality of traces is oriented transverse to the fold line.

15. The apparatus of claim 10 wherein the energy delivery device is included in a treatment tip that is configured to be detachably coupled with a handpiece.

16. The apparatus of claim 10 wherein the flexible circuit includes a treatment electrode configured to emit high frequency electromagnetic energy in the radio-frequency band of the electromagnetic spectrum, and the first plurality of traces connect the first terminal of the electronic component with the treatment electrode.

17. The apparatus of claim 10 wherein the flexible circuit includes a first attachment pad and a second attachment pad, the first terminal of the electronic component is attached to the first attachment pad, each of the first plurality of traces terminates at the first attachment pad, the second terminal of the electronic component is attached to the second attachment pad, and each of the second plurality of traces terminates at the second attachment pad.

18. The apparatus of claim 17 wherein the flexible circuit includes a first contact pad and a second contact pad, each of the first plurality of traces extends from the first attachment pad to the first contact pad, the first contact pad is configured to establish an external contact with the first terminal, each of the second plurality of traces extends from the second attachment pad to the second contact pad, and the second contact pad is configured to establish an external contact with the second terminal.

* * * * *